(12) United States Patent
Mitchell et al.

(10) Patent No.: US 8,564,449 B2
(45) Date of Patent: Oct. 22, 2013

(54) OPEN CIRCUIT WEAR SENSOR FOR USE WITH A CONDUCTIVE WEAR COUNTERFACE

(75) Inventors: David J. Mitchell, Oviedo, FL (US); Anand A. Kulkarni, Oviedo, FL (US)

(73) Assignee: Siemens Energy, Inc., Orlando, FL (US)

( * ) Notice: Subject to any disclaimer, the term of this patent is extended or adjusted under 35 U.S.C. 154(b) by 945 days.

(21) Appl. No.: 12/685,766

(22) Filed: Jan. 12, 2010

(65) Prior Publication Data

US 2011/0169651 A1    Jul. 14, 2011

(51) Int. Cl.
*G08B 21/00* (2006.01)

(52) U.S. Cl.
USPC ........... 340/679; 340/454; 340/664; 340/677; 73/146

(58) Field of Classification Search
USPC .............. 340/679, 454, 664, 677; 73/146, 86, 73/104
See application file for complete search history.

(56) References Cited

U.S. PATENT DOCUMENTS

| | | | |
|---|---|---|---|
| 4,390,870 A | 6/1983 | Michael | |
| 4,520,661 A | 6/1985 | Tamai | |
| 4,562,421 A | 12/1985 | Duffy | |
| 4,642,557 A | 2/1987 | Ross | |
| 4,744,241 A * | 5/1988 | Mayer | 73/104 |
| 5,015,990 A * | 5/1991 | Reede | 340/454 |
| 6,838,157 B2 | 1/2005 | Subramanian | |
| 7,270,890 B2 | 9/2007 | Sabol | |
| 2004/0202886 A1 | 10/2004 | Subramanian | |
| 2005/0198967 A1 | 9/2005 | Subramanian | |
| 2006/0056960 A1 | 3/2006 | Sabol | |

* cited by examiner

*Primary Examiner* — Hoi Lau (57) ABSTRACT

A component including a surface subject to wear by an electrically conductive wear counterface (50). The component comprises a substrate (10); one or more material layers (32) overlying the substrate (10); a wear surface layer (16) overlying the one or more material layers (32); a first pair of spaced apart and electrically open wear sensor conductors (12/14) disposed in the substrate (10), in the one or more material layers (32), or in the wear surface layer (16); a first wear warning electrical circuit (68/69/70/74) for communicating with the first pair of conductors (12/14) for providing a first wear warning; and wherein when the wear counterface (50) has worn overlying layers, the wear counterface (50) interconnects the first pair of conductors (12/14) to activate the first wear warning circuit (68/69/70/74).

25 Claims, 5 Drawing Sheets

OPEN CIRCUIT WEAR SENSOR FOR USE WITH A CONDUCTIVE WEAR COUNTERFACE

FIELD OF THE INVENTION

This invention relates to sensors for detecting surface wear in one or both contacting surfaces of a machine, where at least one of the contacting surfaces comprises a conductive material.

BACKGROUND OF THE INVENTION

Relative motion between contacting components in a machine (e.g., high performance machines or engines) can result in excessive wear of one or both components. For example, components subjected to high frequency and low frequency vibrations may result in excessive wear of component attachments or mating surfaces. The component wear, if left undetected, can cause component and machine malfunctions. For example, spring clips in combustion turbine engine experience surface wear from contact with other components due to operational vibrations and dynamic forces.

In some applications, component wear can be controlled to acceptable levels by using lubricants, by employing materials with high resistance to wear and/or by design features that limit motion and contact and resulting component wear. However, there are many situations where relative motion cannot be eliminated, such as in brake linings, meshing gears, contacting sliders and slip fits; wear is unavoidable in such applications.

Knowledge of the wear condition of critical components can be used to avoid forced outages due to unexpected component failures. Such knowledge also enables the machine to be shut down for repair of the worn components at a convenient scheduled time, rather than continuing operation until a component is worn beyond repair or an emergency shut down is required. Significant costs can be saved by both avoiding forced outages and by ensuring the worn parts can be repaired instead of scrapped when a scheduled outage is performed.

The extent of wear and the suitability of the component for continued service can be determined by visual and/or dimensional inspection. In some applications, wear indicators are embedded within or proximate one or more of the contacting surfaces. For example, in the context of brake linings, wear limit notches or "squealers" generate an audible warning when a predetermined amount of lining wear has occurred.

However, there are many applications where periodic inspection is not feasible due to such factors as, for example, time and labor expenses, cost of inspection and operational disruptions due to inspection down time. In addition, visual and audible warnings are not always feasible monitoring solutions, as is the case when monitoring internal components of a gas turbine engine. Thus, there is a need for a system that can monitor component wear while the component is in an operational state.

Wear sensors mounted in one or both of the wearing components can advantageously provide real-time monitoring of component wear during machine operation. These sensors measure the amount of wear that occurs in regions prone to wear and notify an operator when a preselected amount of wear has occurred. The sensors improve machine reliability and enable more accurate maintenance planning. Such monitoring also improves safety and reduces operating and maintenance costs by indicating a maintenance requirement before any component damage occurs. Real time wear monitoring also avoids unscheduled outages.

A conductive wear sensor is described in commonly-owned U.S. Pat. No. 7,270,890, entitled, Wear Monitoring System with Embedded Conductors. The patent describes a sensor comprising a closed circuit conductive trace that is transformed to an open circuit condition when a counterface wears through the conductive trace. While this sensor has many applications, frequently both members of a wear couple (i.e., two components in contact along the wear surface) are electrically conductive metals. An open circuit cannot be detected in such an electrically conductive component.

BRIEF DESCRIPTION OF THE DRAWINGS

The invention is explained in the following description in view of the drawings that show.

DETAILED DESCRIPTION OF THE INVENTION

Before describing in detail the particular methods and apparatuses related to an open circuit wear sensor for use with a conductive counterface in accordance with various aspects of the present invention, it should be observed that the present invention, in its various embodiments, resides primarily in a novel and non-obvious combination of hardware and method steps. Accordingly, the hardware and method steps have been represented by conventional elements in the drawings, showing only those specific details that are pertinent to the present invention so as not to obscure the disclosure with details that will be readily apparent to those skilled in the art having the benefit of the description herein.

The following described embodiments are not intended to define limits of the structures or methods of the invention but to provide only exemplary constructions. The embodiments are permissive rather than mandatory and illustrative rather than exhaustive.

According to the present invention, an open circuit wear sensor, comprising for example two proximate wear sensor conductors configured in an open-circuit arrangement, is formed in a dielectric substrate or a conductive substrate. In the latter application, the wear sensor conductors are insulated from the conductive substrate. In either case, a dielectric layer (a wear surface or wear coating) is formed over the wear sensor conductors and when the wear surface is worn by a conductive wear counterface, the conductors are exposed and the counterface interconnects (bridges) or shorts the conductors. This action completes a circuit and provides an indication (a wear indication) that the wear surface has been breached.

Generally, the wear surface (also referred to as a wear resistant coating or simply a wear coating) is defined as the outermost material layer that contacts the wear counterface. A material of the wear surface may be conductive or insulative. As applied to the present invention, in the former situation, the wear sensor conductors are insulated from the conductive material of the wear surface. In any case, the wear sensor conductors of the present invention are disposed below the wear surface, within the wear surface, within the substrate or within a material layer between the substrate and the wear surface.

A wear indicator connected to the conductors is energized only when the dielectric material is breached and the wear sensor conductors are shorted by the wear counterface. The wear indicator is not energized when the conductors are open.

The wear sensor conductors may be deposited on or within any coated or uncoated substrate material, on or within any material layer, or within the wear layer material. For example, the wear sensor conductors may be disposed with a trench formed in the material. Although a material of the substrate and the wear layer may be conductive or insulative as described above, a material of the wear counterface must be electrically conductive (or comprise an electrically conductive region) to short the conductors and activate the wear indicator.

Figure 1:
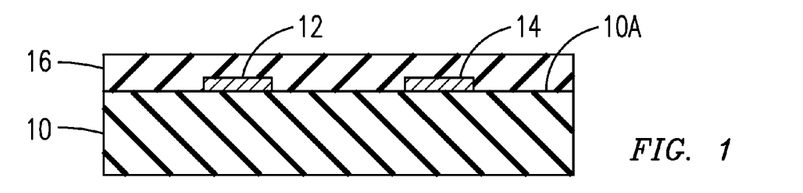
FIGS. 1-3 illustrate three different embodiments according to the present invention.

FIG. 1 illustrates a cross-sectional view of a dielectric substrate 10 and normally-open proximate wear sensor conductors 12 and 14, two elements of a wear sensor, formed on an upper surface 10A of the substrate 10. A dielectric wear surface layer 16 (the wear surface layer may also be referred to as a wear resistant coating layer) is formed over the upper surface 10A and the conductors 12 and 14. A wear counterface (not illustrated) wears the wear surface 16 during operation of the substrate 10, shorting the conductors 12 and 14 to close an external circuit and operate the wear indicator, as further described below.

Figure 2:
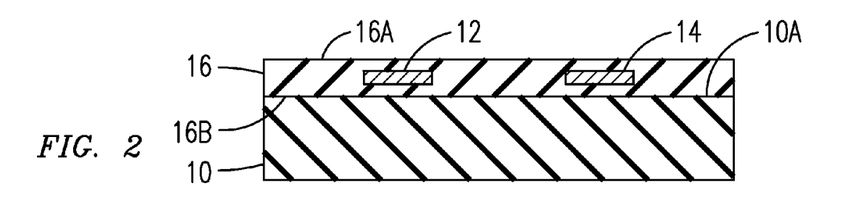

In another embodiment, the conductors 12 and 14 are disposed within the wear surface 16 between an upper wear surface 16A and a lower wear surface 16B. See FIG. 2. In yet another embodiment, the conductors 12 and 14 are disposed within, over or under a material layer disposed between the upper surface 10A of the substrate 10 and the lower wear surface 16B of the wear surface 16.

Figure 3:
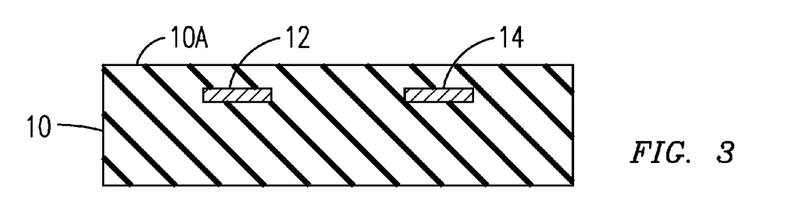

FIG. 3 illustrates the wear sensor conductors 12 and 14 embedded within the non-conductive substrate 10. The surface 10A is worn by the wear counterface until the conductors are exposed and the wear counterface interconnects or shorts the conductors 12 and 14 to activate the wear indicator as explained below.

Figures 4, 5, 6:
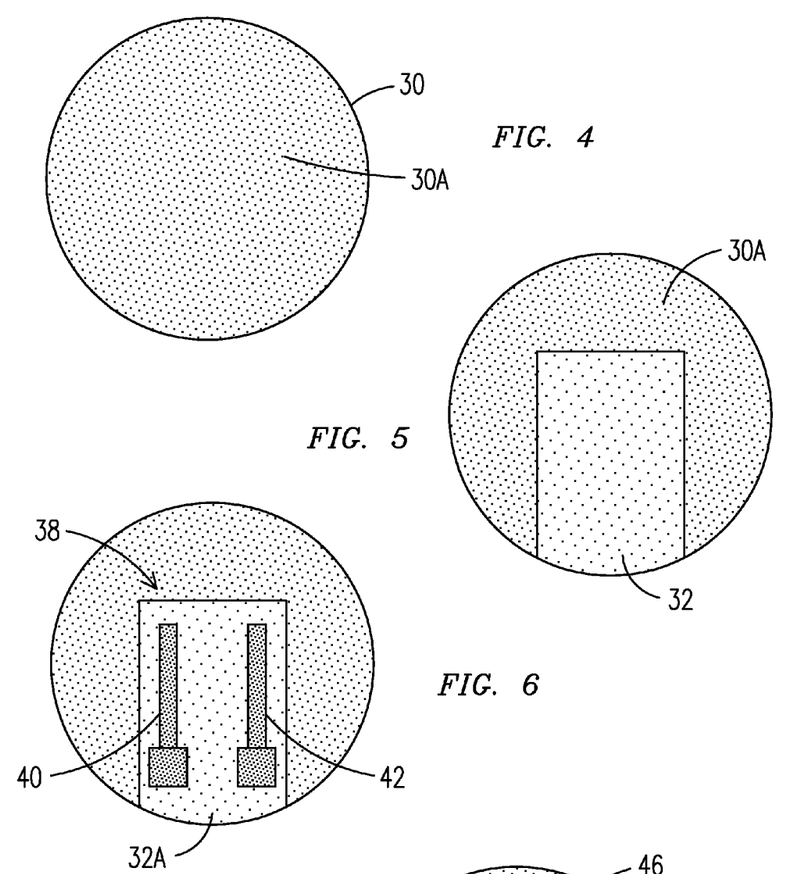
FIGS. 4-7 illustrate successive steps of a process for applying a wear sensor of the present invention to a substrate.

FIG. 4 begins a sequence of figures illustrating process steps for fabricating the normally-open circuit wear sensor conductors on or within a conductive substrate according to the present invention. FIG. 4 illustrates an exposed surface 30A of a conductive substrate 30 or a conductive coating overlying a substrate. The exposed wear surface 30A is worn during operation of the substrate and thus wear sensor conductors are formed on or embedded within the exposed surface 30A, suitably insulated from the conductive substrate.

Figure 8:
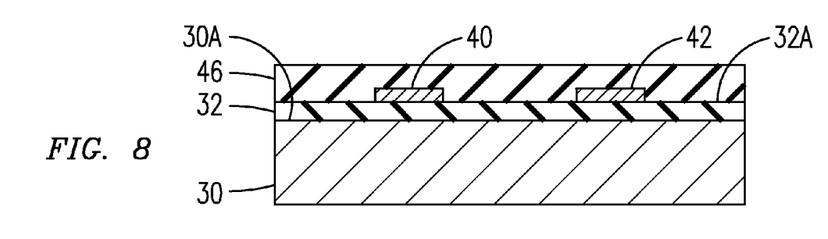
FIG. 8 illustrates a cross-sectional view of a substrate including the wear sensor of the present invention.

As illustrated in FIG. 5, a dielectric material region 32 is formed on the exposed surface 30A. In one embodiment the dielectric region 32 is about 1-10 mils thick. See also the cross-sectional view of FIG. 8.

A wear sensor 38 comprising two wear sensor conductors 40 and 42, see FIG. 6, is formed on an upper surface 32A of the dielectric material region 32. In one embodiment a thickness of material forming each conductor 40 and 42 is about 1-6 mils.

A dielectric layer 46 (which can serve as the wear surface layer or wear coating) is formed over the wear sensor conductors 40 and 42 and completely or partially over exposed regions of the upper surface 32A. See FIGS. 7 and 8. A thickness of the dielectric layer 46 is selected responsive to the wearability of the dielectric layer material, wear characteristics of the wear counterface and the amount of contact force developed between the dielectric layer 46 and the wear counterface during operation. Preferably, material of the wear surface layer 46 can be removed (by machining back the layer 46 for example) such that the wear surface layer 46 has a desired thickness.

Figure 7:
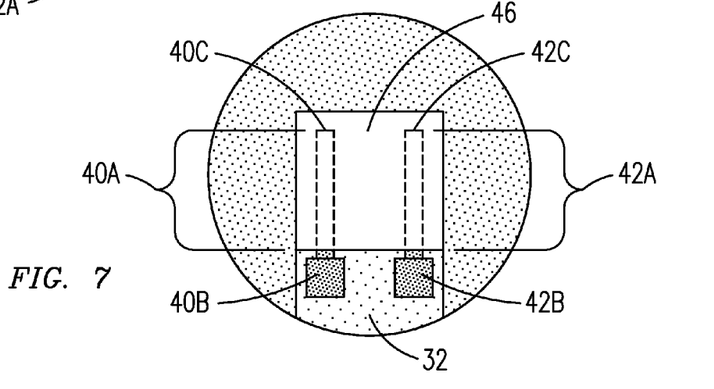

As shown in FIG. 7, the dielectric layer 46 covers a region 40A and 42A of each conductor while regions 40B and 42B are exposed to form connection regions for connecting additional wear sensor components as described below.

Although end regions 40C and 42C of the conductors 40 and 42 are illustrated in FIG. 7 as terminating proximate end regions of the dielectric material region 32, according to other embodiments the conductors extend to end regions of the substrate 30 when suitably insulated from any substrate conductive material they may contact. In these embodiments the conductors may be considered as extending beyond boundaries of the wear sensor 38.

Figure 9:
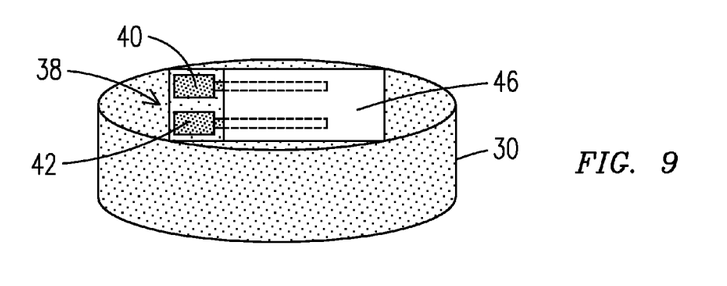
FIGS. 9-11 illustrate wear stages of a substrate surface caused by motion of a wear counterface.
Figure 10:
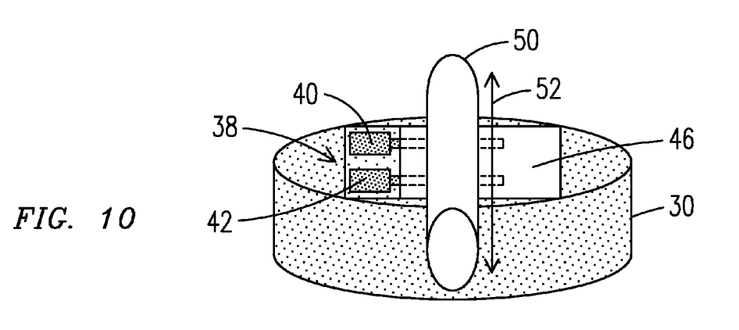
Figure 11:
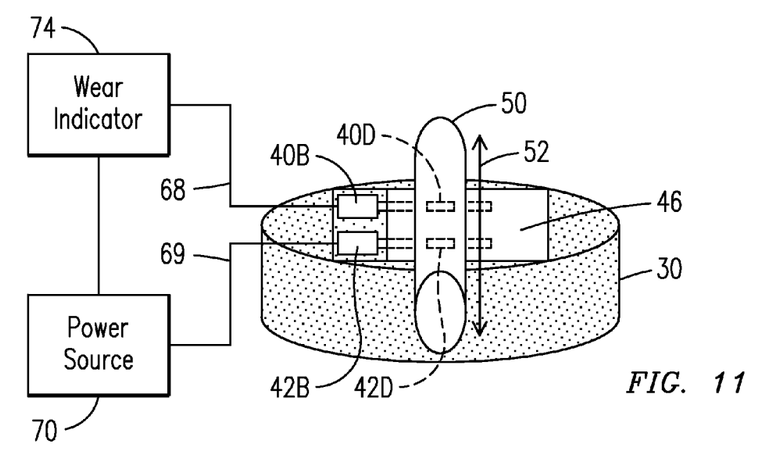

FIGS. 9-11 illustrate operation of the wear sensor of the present invention. FIG. 9 depicts the wear sensor 38 and the substrate 30. Before wear occurs the dielectric layer 46 (which may also act as a wear surface layer or wear coating) is intact.

FIG. 10 illustrates an orientation of an electrically conductive wear counterface 50 relative to the substrate 30 and a direction of wear motion indicated by an arrowhead 52. Although a cylindrical wear counterface is illustrated, this is not required as the wear counterface can have any shape, e.g., a cylinder or a flat surface. It is only required that during operation, the substrate 30 and the wear counterface 50 contact along a line or a plane. A point-wear contact, such as a sphere contacting a flat surface, may not provide the desired functionality of the present invention as the sphere may not be able to contact and interconnect the wear sensor conductors. The line or plane contact interface enables the wear counterface 50 to simultaneously contact (and short together) both conductors 40 and 42.

Figure 12:
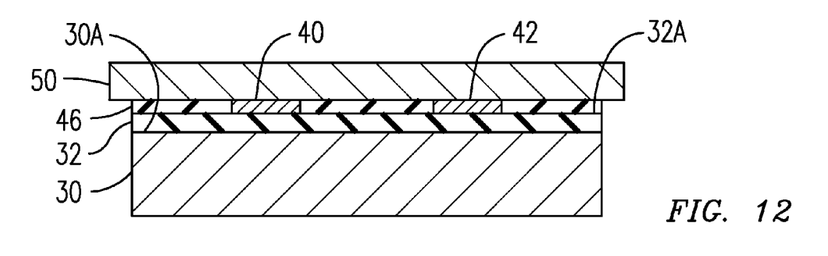
FIG. 12 illustrates a cross-sectional view of a substrate worn by a wear counterface.

When the dielectric wear surface layer 46 is worn through, see FIGS. 11 and 12, regions 40D and 42D of the respective wear sensor conductors 40 and 42 are exposed and simultaneously contacted by the electrically conductive wear counterface 50. This action completes a circuit including a power source 70 and a wear indicator 74. When energized, the wear indicator 74 indicates that wear of the dielectric wear surface layer 46 has reached to the depth of the wear sensor conductors 40 and 42. As shown in FIG. 11, conductors 68 and 69 associated with the power source 70 and the wear indicator 74 are connected to the regions 40B and 42B of the respective conductors 40 and 42.

According to another embodiment, the conductors 68 and 69 are not required, as a wireless transceiver is connected to the regions 40B and 42B for transmitting a wireless signal when the wear conductors 40 and 42 are shorted by the wear counterface. The signal is received by an external receiver for activating a wear indicator.

A material of the substrate 30 may comprise a dielectric or a metal, as described above, or another material such as a ceramic or ceramic matrix composite. An appropriate deposition process for forming the wear sensor conductors on these substrate materials may be accordingly selected, as is known in the art.

Figure 13:
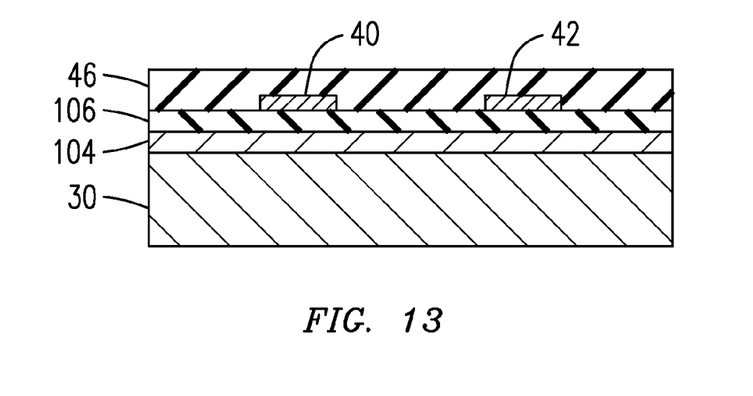
FIGS. 13-19 illustrate cross-sectional views of various embodiments of wear sensors for different applications.

In an application where a conductive layer 104 (see FIG. 13) is disposed over the substrate 30, the wear sensor conductors 40 and 42 are formed in a dielectric layer 106 (i.e., in a trench in the dielectric layer 106) or above the dielectric layer 106 (as illustrated in FIG. 13), that insulates the wear sensor conductors 40 and 42 from the conductive layer 104. The wear surface 46 is formed over the wear sensor conductors 40 and 42. As in the embodiments described above, the wear surface 46 is worn away by contact with the wear counterface (not shown in FIG. 13).

Figure 14:
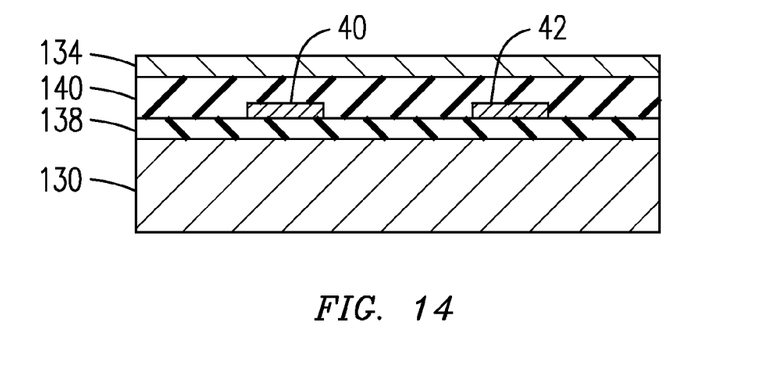

FIG. 14 illustrates an application where a substrate 130 and a wear surface 134 both comprise an electrically conductive material. A dielectric layer 138 and a dielectric layer 140 are interposed between the substrate 130 and the wear surface 134. The wear sensor conductors 40 and 42 are disposed over the dielectric layer 138 and within the dielectric layer 140. The dielectric layer 138 insulates the conductors 40 and 42 from the conductive substrate 130. The dielectric layer 140 insulates the conductors 40 and 42 from the conductive wear surface 134. As in the other presented embodiments, the wear counterface wears the wear surface 134 and the dielectric layer 140, completing a circuit between the wear sensor conductors 40 and 42 to provide a wear indication.

In an alternative embodiment the wear sensor conductors are disposed within a trench formed in the dielectric layer 138.

The wear sensor conductors of the present invention may be deposited on the substrate or within the wear-resistant layer (e.g., a metal, ceramic, or cerment coating) or another material layer using a thin film deposition process such as plasma spraying, electron beam physical vapor deposition, chemical vapor deposition, pulsed laser deposition, mini-plasma, cold spray, direct-write, mini high velocity oxy-fuel, or solution plasma spraying, for example.

In certain applications of the present invention the substrate is fixed while the wear counterface moves while in contact with the substrate. Since the wear counterface closes a conductive path between the two wear sensor conductors disposed within the stationary substrate, it is unnecessary to construct an electrical circuit (with attendant conductors) within the moving wear counterface and connect that circuit to external electrical devices (e.g., a power source and a wear indicator). This invention thus avoids the use of elements typically employed to electrically connect to a moving or rotating element, (e.g., brushes and slip rings). All installation and maintenance actions related to the wear sensor conductors are performed on the stationary substrate.

The various sensor conductors described herein may be formed as follows.
1. If the substrate has a high dielectric constant, as with an insulating ceramic such as $Al_2O_3$, the sensor conductors may be deposited directly on the substrate as illustrated in FIG. 1.
2. If the substrate does not exhibit a sufficiently high dielectric constant, an electrically insulating layer or dielectric layer is formed on the substrate surface using a material such as an oxide ceramic with high dielectric/insulating properties e.g., $Al_2O_3$, Yttria-stabilized Zirconia (YSZ), and $MgAl_2O_4$.
3. After completing step 1. or 2., the sensor conductors are deposited using an electrically conducting material with a high oxidation resistance at the operational temperature of the substrate and the counterface. For example Ni—Cr is electrically conducting and suitable for operation to about 500° F. (260° C.). This material is therefore suitable for use with a gas turbine combustor spring clip assembly operating below the 500° F. threshold. In this application, an exemplary sensor conductor thickness is in a range of about 10-50 microns, with 10-25 microns a preferred thickness in one embodiment. The wear sensor conductors may be formed by subtractive etching of a conductive surface or application of electrically conductive materials, for example by spraying.
4. Optionally a wear coating, such as an alloy of $Cr_2C_3$—NiCr or WC—Co, or commercial products known as Stellite 6B or T800 is deposited over the sensor conductors.

In another embodiment, a trench or groove 160 is formed in a wear substrate 162 for receiving wear sensor conductors 170 and 172. See FIG. 15. The wear substrate 162 further comprises a wear surface 174. A width $W_1$ of the trench or groove 160 is smaller than a width $W_2$ of the wear surface 174 to minimally impact the wear behavior of the wear substrate 162 and the wear surface 174.

Figure 15:
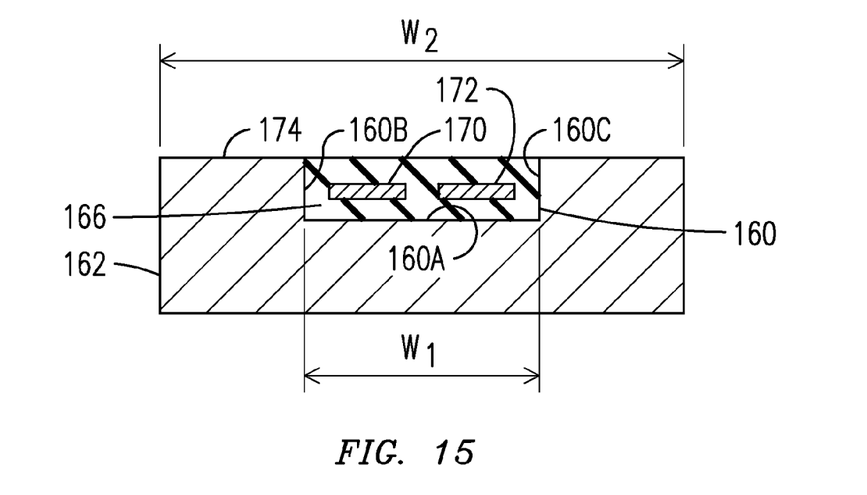

If the wear substrate 162 comprises conductive material, a trench bottom region 160A and trench sidewall regions 160B and 160C comprise an electrically insulating material 166 that insulates the wear sensor conductors 170 and 172 from each other and from the conductive substrate 162.

Figure 16:
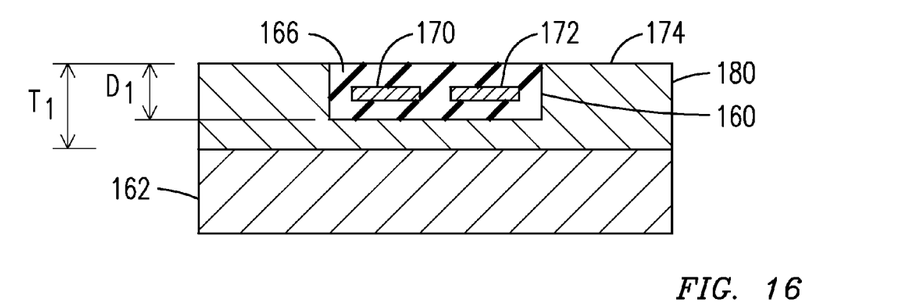

In FIG. 16 a conductive wear coating layer 180 overlies the wear substrate 162, with an exposed surface of the wear coating layer 180 forming the wear surface 174. The trench or groove 160 is disposed in the wear coating layer 180 as illustrated. In this embodiment a depth $D_1$ of the trench 160 is less than a thickness $T_1$ of the wear coating layer 180 to minimize impact on the wear behavior of the wear coating layer 180.

In both the FIGS. 15 and 16 embodiments after the trench or groove 160 is formed, a dielectric material is formed in the trench 160 by any means known to those in the art, such as thermal spray, solution spray, direct-write, vapor deposition, or slurry casting to coat the bottom surface 160A and the sidewall surfaces 160B and 160C. Conductive traces are formed to serve as the wear sensor conductors 170 and 172 and additional dielectric material is formed over the conductive traces. The exposed surface of the dielectric material may be machined flush with the wear surface 174.

In the embodiments of FIGS. 15 and 16 if the wear substrate 162 and/or the wear coating layer 180 are not electrically conductive, it is not required that the material 166 comprise an electrically insulating material.

Figure 17:
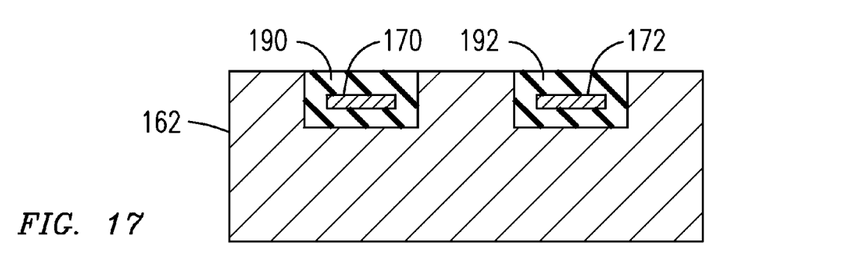

In yet another embodiment, the wear sensors 170 and 172 are formed in separate trenches 190 and 192 in the substrate 162, as illustrated in FIG. 17.

Figure 18:
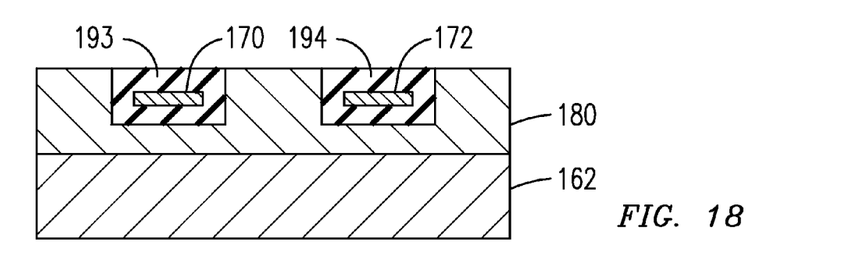

In still another embodiment, the wear sensors 170 and 172 are formed in separate trenches 193 and 194 in the wear coating layer 180, as illustrated in FIG. 18.

In yet another embodiment, the wear sensor comprises two pairs of wear sensor conductors, each conductor pair formed at a different depth below a surface of the coating or a surface of the substrate. See FIG. 19.

Figure 19:
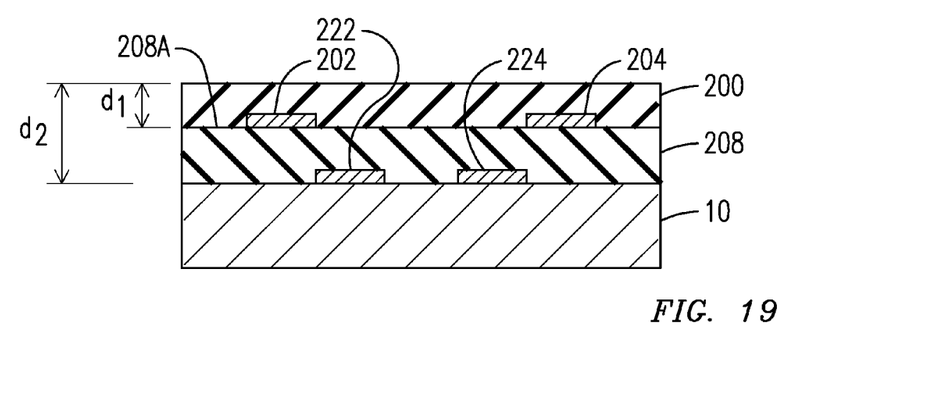

When a material layer 200 above a first or upper-most conductor pair 202 and 204 is breached, the counterface shorts or interconnects the first conductor pair 202 and 204 and closes an electrical circuit to actuate a first wear indicator, indicating that the material layer 200 has worn to a depth d1. A top surface 208A of a material layer 208 is now exposed. When the wear counterface wears the first conductor pair 202 and 204 and wears a portion of the material layer 208 above a second conductor pair 222 and 224 a different electrical path is completed when the wear counterface interconnects the conductors 222 and 224. This action energizes a second wear indicator indicating the material layer 208 has been worn to a depth d2. Additional conductors can be disposed at different depths to provide a graded indication of the wear depth. Different maintenance actions can be performed depending on the depth of material wear.

The teachings of the present invention can also be employed where two contacting or proximate components vibrate, the vibrations bringing the two components into contact and wearing one or both of the components.

The teachings of the present invention can also be employed in a system where two components are in a close proximal relationship during normal operation. Operational anomalies cause the two components to contact, which can lead to operational difficulties. The conductive sensors of the present invention are formed in a first one of the components and when contacted by a second component, the conductive sensors are shorted and an alarm activated. In this application it may advisable to form the conductive sensors in a trench as illustrated in FIGS. 15 and 16 or in two trenches as illustrated in FIGS. 17 and 18. As the top surface of the conductive sensors is worn away, additional conductive sensor material is available to provide the contact alarm.

In yet another embodiment, it may be desirable to orient the wear conductor sensors relative to a direction of motion of the wear counterface to preclude any smearing of the material of the conductor sensors. Such smearing may bridge the gap between the conductors, shorting the conductors and obviating the shorting function of the wear counterface.

Thickness dimensions are set forth herein for certain of the material layers. However, it is recognized that these dimensions are not critical to the functionality of the present invention. The thickness of the wear sensor conductors (e.g., conductors 40 and 42) is also not critical to the functionality of the present invention, except that a duration of the short (as determined by a thickness of the conductors before the conductors are completely destroyed by wearing) must be sufficiently long to provide an indication of the short, thereby warning that the wear surface has worn away.

The various material layers described above according to the various embodiments may comprise a thermal barrier layer, a substrate layer, a dielectric layer, a wear coating layer (a wear resistive coating or a wear surface), a conductive layer, a ceramic layer or any other layers known in the art. A material of each of these layers may be selected based on the application, proximate materials, and expected wear affects of the wear counterface. Also, material layers below the wear surface are selected based on the application and the proximate layer materials.

As used herein the terms "open" and "short" when applied to electrical circuits do not require a respective infinite resistance and a zero resistance. The terms are intended to suggest a very high resistance (e.g., greater than about several megaohms) through which little current flows or a very low resistance (e.g., less than about 100 ohms) through which a considerable current flows. The actual values of resistance and current in any particular application are dependent on the materials comprising the conductors, the substrate and the wear counterface and on the configuration of the electrical circuit. Also, the term "interconnect" as used herein requires a connection between two conductors through which current can flow. An interconnect does not necessarily require a short circuit.

One application for the present invention includes a gas turbine having rotating turbine blades that may wear a surrounding shroud. Mounting the wear sensor of the present invention in material layers comprising the shroud provides a wear warning when the shroud has been worn by the blades to a depth of the wear sensor.

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims.

The invention claimed is:

1. A component including a surface subject to wear by an electrically conductive wear counterface, the component comprising:
   a substrate;
   one or more material layers overlying the substrate;
   a wear surface layer overlying the one or more material layers;
   first and second spaced apart and coplanar wear sensor conductive pads formed by a conductive material deposition process, the first and the second pads electrically insulated from each other and each comprising first and second regions, each first region disposed in the substrate, in the one or more material layers, or in the wear surface layer and each second region exposed along a surface of the component;
   a wear warning electrical circuit connected to the second regions; and
   wherein when the wear counterface has worn overlying layers, the wear counterface contacts the first regions to activate the wear warning circuit.

2. The component of claim 1 wherein the first regions and the wear counterface contact along a line or in a plane.

3. The component of claim 1 wherein when the first and the second conductive pads are disposed in a conductive material, the component further comprises one or more insulating regions insulating the first and the second conductive pads from the conductive material.

4. The component of claim 1 wherein the substrate is fixed and the wear counterface moves relative to the substrate.

5. A component including a surface subject to wear by an electrically conductive wear counterface, the component comprising:
   a substrate;
   one or more material layers overlying the substrate;
   a wear surface layer overlying the one or more material layers;
   a first pair of spaced apart and electrically open wear sensor conductors disposed in the substrate, in the one or more material layers, or in the wear surface layer;
   a first wear warning electrical circuit for communicating with the first pair of conductors for providing a first wear warning;
   wherein when the wear counterface has worn overlying layers, the wear counterface interconnects the first pair of conductors to activate the first wear warning circuit; and
   wherein the first pair of conductors are disposed at a first depth below the surface subject to wear, the component further comprising a second pair of spaced apart and electrically open wear sensor conductors disposed in the substrate, in the one or more material layers, or in the wear surface layer at a second depth below the surface subject to wear, the second depth different from the first depth, a second wear warning electrical circuit for communicating with the second pair of conductors for providing a second wear warning, and wherein when the wear counterface has worn overlying layers the wear counterface interconnects the second pair of conductors to activate the second wear warning circuit.

6. The component of claim 1 wherein the wear counterface is subjected to vibrations relative to the substrate.

7. The component of claim 1 wherein the first and the second conductive pads are oriented relative to motion of the wear counterface to limit smearing of material of one of the first and the second conductive pads in a direction toward the other of the first and second conductive pads.

8. The component of claim 1 further comprising a wireless transmitter for transmitting a signal indicative of wear when the wear counterface contacts the first regions.

9. The component of claim 1 wherein the first and the second pads are disposed in a trench formed in the substrate, in a trench formed in the one or more material layers, or in a trench formed in the wear surface layer.

10. The component of claim 9 wherein the trench is formed in a dielectric material.

11. The component of claim 9 wherein the trench is formed in a conductive material and the component further comprises dielectric material insulating the first and the second pads from the conductive material.

12. The component of claim 1 wherein the first wear sensor pad is disposed in a first trench and the second wear sensor pad is disposed in a second trench, the first and the second trenches formed in the substrate, formed in the one or more material layers or formed in the wear surface layer.

13. The component of claim 12 wherein the first and second trenches are formed in a dielectric material.

14. The component of claim 12 wherein the first and second trenches are formed in a conductive material and the component further comprises first dielectric material insulating the first pad from the conductive material and second dielectric material insulating the second pad from the conductive material.

15. The component of claim 1 wherein a thickness of first and second pads is selected to activate the wear warning circuit for a desired duration.

16. The component of claim 1 wherein the wear warning circuit is external to the component.

17. A component comprising:
a wear surface in at least intermittent contact with a wear counterface such that the wear surface wears in a direction of wear;
first and second spaced apart and coplanar conductive pads formed by a conductive material deposition process below the wear surface, the first and the second conductive pads electrically insulated from each other and each comprising first and second regions, each second region exposed along a surface of the component; and
a circuit connected to the second regions for providing an indication of wear when the wear counterface wears the wear surface sufficiently to contact the first regions and activate the circuit.

18. The component of claim 17, further comprising:
a substrate;
a wear coating on the substrate to define the wear surface; and
the first and the second conductive pads formed within the wear coating.

19. The component of claim 18, wherein the first and the second pads are disposed on a surface of the substrate, the wear coating overlying the surface of the substrate.

20. The component of claim 18, wherein the first and the second pads are disposed on a surface of or within a dielectric layer overlying a surface of the substrate.

21. A component including a wear surface subject to wear by an electrically conductive wear counterface, the component comprising:
an electrically conductive substrate having at least one trench formed therein, an exposed surface of the substrate comprising a wear surface;
first and second spaced apart conductive pads disposed in the at least one trench and below the wear surface, the first and the second pads electrically insulated from each other and formed by a conductive material deposition process, each one of the conductive pads comprising coplanar first and second regions, the second regions exposed along a surface of the component;
a dielectric material disposed between the first conductive pad and trench surfaces and between the second conductive pad and trench surfaces;
a wear warning electrical circuit connected to the second regions and
wherein when the wear counterface has worn the wear surface to expose the first region of each of the first and second pads, the wear counterface contacts the first region of the first and second pads to activate the wear warning circuit.

22. The component of claim 21 wherein the at least one trench comprises a single trench with the first and the second pads disposed in the single trench.

23. The component of claim 21 wherein the at least one trench comprises a first and a second trench, wherein the first pad is disposed in a first trench and the second pad is disposed in a second trench.

24. The component of claim 5 wherein at least one of the first and the second wear sensor conductors is disposed in a trench defined in the substrate, in the one or more material layers, or in the wear surface layer.

25. The component of claim 24 further comprising an insulating material between the at least one of the first and the second pair of wear sensor conductors and the substrate, the one or more material layers or the wear surface layer.

* * * * *